United States Patent [19]

Hanson

[11] Patent Number: 5,120,218
[45] Date of Patent: Jun. 9, 1992

[54] ORTHODONTIC TRACTION DEVICES

[76] Inventor: G. Herbert Hanson, 57 Augusta St., Hamilton, Ontario, Canada, L8N 1P8

[21] Appl. No.: 699,114

[22] Filed: May 13, 1991

[51] Int. Cl.$^5$ .............................................. A61C 3/00
[52] U.S. Cl. ..................................................... 433/19
[58] Field of Search ........................ 433/17, 18, 19, 21

[56] References Cited

U.S. PATENT DOCUMENTS

| | | | |
|---|---|---|---|
| 3,618,214 | 11/1971 | Armstrong | 433/19 |
| 3,798,773 | 3/1974 | Northcutt | 433/19 |
| 4,462,800 | 7/1984 | Jones | 433/19 |
| 4,551,095 | 11/1985 | Mason | 433/19 |
| 4,618,324 | 10/1986 | Nord | 433/19 |
| 4,708,646 | 11/1987 | Jasper | 433/19 |
| 4,969,822 | 11/1990 | Summer | 433/19 |

Primary Examiner—Cary E. O'Connor
Attorney, Agent, or Firm—Rogers & Scott

[57] ABSTRACT

New orthodontic traction devices that can be pre-assembled or custom assembled in the operatory using connector members consisting of cut lengths of metal spring material or wire rope material uses attachment members each of which has a recess into which the respective end of the spring or rope material is inserted. The attachment member is crimped radially inward to plastically deform the metal into the helical grooves in the connector member external surfaces and thus retain the end; alternatively the end can be secured by brazing or cementing. If spring material is used the attachment member has a central boss which protrudes into the spring. An eyelet attachment member is non-removable from an anchor hook, except by the orthodontist, by making the tongue with the eyelet hole too thick to pass through the hook mouth, while the tongue end-most border portion can pass through, so that the eyelet must be rotated to a required attitude before it can be placed on or removed from the hook. A hooked attachment member used with an enlarged-head anchor pin is non-removable by arranging that the attachment member body fouls the anchor body unless they are in required relative attitudes. Other forms of eyelet hole and hook and a ball and socket attachment system are also disclosed.

34 Claims, 8 Drawing Sheets

ORTHODONTIC TRACTION DEVICES

FIELD OF THE INVENTION

The present invention is concerned with improvements in or relating to traction devices as employed in orthodontic procedures, such devices each comprising a connection member of appropriate length having two attachment members fastened to its respective ends by which it is attached to respective anchor members provided by other orthodontic devices.

REVIEW OF THE PRIOR ART

Traction devices of various types are used in orthodontic procedures to produce desired tooth and jaw movements, and for that purpose must be attached at their ends between two spaced orthodontic devices constituting respective anchor members and providing respective anchor points, such as between any two of a bracket or a buccal tube attached to a tooth, a hook or an arch wire. In one such traction device known hitherto the connection member is a spring provided at its two ends with eyelets, or their equivalent, which cooperate with respective hooks on respective orthodontic devices attached to the arch wire or to the teeth. Owing to the wide variety of spring lengths and tensions that may be required it is not easy to provide a series of springs of fixed length and tension characteristics, and systems have therefore been developed with which the orthodontist is supplied with a length of the spring material and a number of separate eyelet members from which springs of custom length can be fabricated in the operatory as required.

Another type of traction appliance that is employed connected in the mouth between two spaced anchor points is intended to correct mandibular malformations, such as extreme overjet. Such an appliance may employ either a traction or a compression spring as the connection member, which may be regarded as an "active" member, or may employ what may be regarded as a "non-active" member, such as a telescoping tube and rod, which serves only to limit the amount of intermaxillary movement without applying any spring force between the jaw members. Both active and non-active devices require that the ends be readily but securely attached to their respective anchoring devices. An example of an "active" device is the "Jasper Jumper" appliance sold by Allener Orthodontic Appliances of Sturtevant, Wis., which uses compression springs, while an example of a "non-active" device is the "Herbst" telescoping appliance sold for example by CorMar Inc. of Salisbury, Md.

It is often found with a particular patient that the procedure is not progressing as fast as expected, based on past experience, and frequently this clearly is due to the fact that the patient is disconnecting the traction device for appreciable periods of time, on the grounds of discomfort and/or appearance. The patient will usually deny that this has been done and it is therefore desirable with such a patient to be able to provide attachment members that are relatively easy for the orthodontist to attach and detach in the operatory, but are difficult if not impossible for the patient to detach and attach at home.

DEFINITION OF THE INVENTION

It is an object of the invention to provide new orthodontic traction devices which permit their economical manufacture, and also their ready custom fabrication as required in the operatory.

It is another object to provide such new devices with attachment members which permit their ready attachment and detachment by the orthodontist in the operatory but inhibit detachment by the patient.

In accordance with the present invention there is provided an orthodontic traction device comprising a length of connection material having grooves formed in at least its exterior cylindrical surface and two end attachment members attached respectively at its two ends:

each attachment member comprising a body having at one end thereof an attachment means for its attachment to an orthodontic anchor member, and having at another end thereof a collar portion having a cylindrical body recess formed therein, the recess being of radial dimension sufficient to snugly receive therein the respective end of the connection member with the collar portion embracing the connection member end;

the attachment member being attached to the connection member either by an interposed adhesive material which has entered into the portions of said helical grooves of the connection member end within the recess, or being attached by material of the body radially compressed inwards into the portions of said helical grooves of the connection member end within the recess;

the attachment being such as to prevent withdrawal of the connection member end from the body recess under tension applied to or by the device.

The connection member may be a piece of hollow helical coiled spring having helical grooves in both its interior and exterior cylindrical surfaces between the butting coils of the spring;

wherein the attachment member body has a cylindrical annular body recess formed between the collar portion and a cylindrical inner body boss portion; and wherein the radially inward compression has forced body material into the portions of the helical grooves in both the interior and exterior cylindrical surfaces of the connection member.

Preferably an end of the boss portion protrudes from the body, and the protruding end has a tapered nose facilitating its insertion into the interior of the hollow spring material. The boss portion may be slightly larger in external diameter than the interior diameter of the hollow spring material, so that insertion of the boss portion into the interior of the spring material causes radially outward expansion thereof and increases the frictional engagement between them.

Alternatively, the connection member may be a piece of wire rope having exterior helical grooves formed between the butting strands thereof.

The attachment member body may have a tongue shaped extension in which the attachment means is formed.

A traction device of the invention may be used in combination with a hook member to which an attachment member thereof is to be attached;

wherein the attachment means comprises an eyelet hole in the tongue extension;

wherein the thickness of the tongue shaped extension is greater than the height dimension of the hook member mouth; and wherein the width of the endmost portion of the tongue which borders the eyelet hole is less than the height dimension of the hook member mouth, so that the attachment member can only be mounted on and dismounted from the hook member with the attachment member in the attitude required to present the tongue shaped extension border to the height dimension of the hook member mouth.

Alternatively a traction device of the invention may be used in combination with another orthodontic device having a headed pin with a smaller diameter shaft as an anchor member;

wherein the attachment means comprises an eyelet hole having a portion of enlarged diameter adjacent to the collar portion through which the head of the headed pin can pass, the eyelet hole having a portion of smaller diameter further from the collar portion through which the head cannot pass but in which the smaller diameter shaft of the headed pin can move longitudinally.

The attachment means may comprise a hook formed in the tongue shaped extension, and may be used in combination with another orthodontic device having a headed pin with a smaller diameter shaft as an anchor member, wherein the hook opening comprises a shaft-receiving slot, and wherein dismounting of the hook from the headed pin is prevented by engagement of the attachment member body with the body of the other device unless the hook is in a predetermined angulation relative to the last mentioned body. The shaft receiving slot may be elongated in the longitudinal direction to permit corresponding longitudinal movement of the hook on the shaft of the headed pin.

A device in accordance with the invention may be used in combination with another orthodontic device having a headed pin with a smaller diameter shaft as an anchor member, wherein an eyelet hole provided in the attachment member is elongated in the longitudinal direction to permit corresponding longitudinal movement of the attachment member on the shaft of the headed pin.

In another device of the invention the attachment member body may be provided adjacent one end with a lingually extending protrusion and a mesially-distally extending arch wire receiving passage is provided in the protrusion; the arch wire receiving passage may taper inwardly from both its ends to be of smaller occlusal-gingival dimension intermediate its ends.

In a further device of the invention the attachment member body may be spherical and the attachment means thereof may comprise a hemispherical surface of the body, and wherein an associated anchor member has a mesial-distal extending passage through which the connector member passes and a distal-opening hemispherical cup into which the spherical body enters to limit the relative mesial-distal movement of the connector and anchor members, while permitting angulation of the connector member relative to the anchor member. When the connector member is a piece of wire rope the part of the connector member not required to pass through the mesical-distal passage may be coated with a plastic material.

DESCRIPTION OF THE DRAWINGS

Particular preferred embodiments of the invention will now be described, by way of example, with reference to the accompanying diagrammatic drawings, wherein.

DESCRIPTION OF THE PREFERRED EMBODIMENTS

Figure 1:
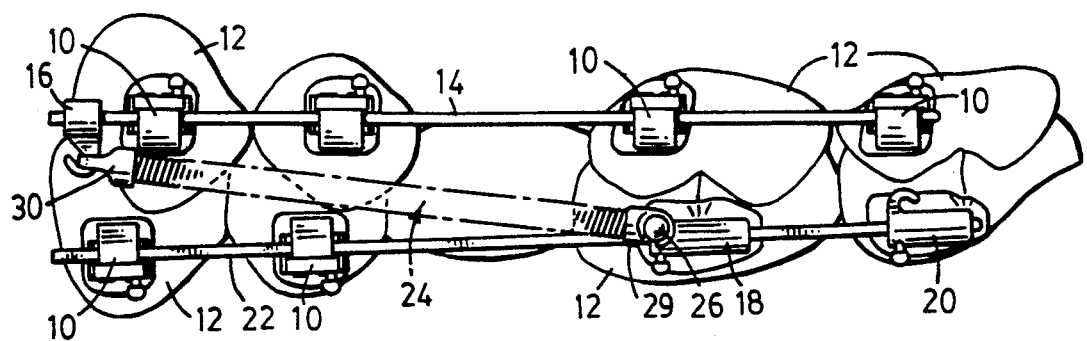
FIG. 1 is a buccal elevation showing a traction spring of the invention as used in an intermaxillary procedure connected between an archwire hook on an upper archwire and a buccal tube attached to a tooth in the lower jaw.

FIG. 1 illustrates a typical use of a helical wire traction spring of the invention in an intermaxillary procedure between upper and lower jaws. An orthodontic bracket 10, for example as disclosed in my prior U.S. Pat. No. 4,492,573, the disclosure of which is incorporated herein by this reference, is attached to each of the four upper teeth 12 that are shown, and to two of the four lower teeth 12 that are shown. The four upper tooth brackets are connected by an upper arch wire 14 on which is mounted an arch wire gripping hook 16. The two lower tooth brackets and two different buccal tubes 18 and 20, which will be described below, are connected by a lower arch wire 22. A connection member consisting of a piece 24 of the helical wire spring is connected between the hook 16 and a headed pin 26 on the buccal tube 18 as respective end anchor members. It is a characteristic of such a helical spring wound from wire that it is hollow and has in its cylindrical exterior and interior surfaces respective helical grooves 28 formed between the butting turns.

Figure 3:
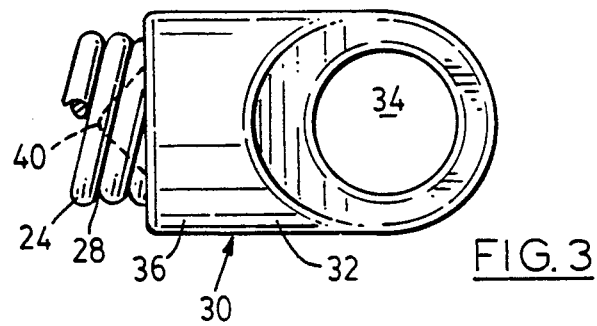
FIG. 3 is a plan view corresponding to FIG. 2 to show the configuration of a tongue shaped extension of the attachment.
Figure 2:
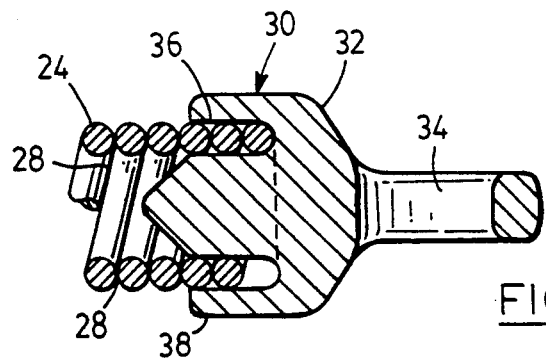
FIG. 2 is a longitudinal cross section through one end of a traction spring assembly employing a helical wire spring prior to the crimping attachment of an eyelet attachment member to one spring end.
Figure 4:
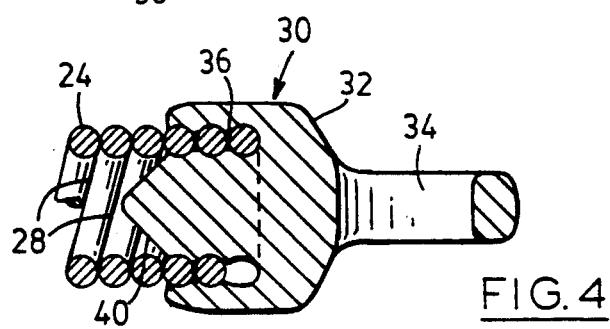
FIG. 4 is a longitudinal cross section corresponding to FIG. 2 and showing the assembly end subsequent to the crimping attachment of the eyelet attachment member to the spring end.

The traction devices can be pre-formed and supplied to the orthodonist in different lengths, or each made to the length required in the operatory by the orthodontist, cuts a piece of the spring material from a longer length thereof and attaches the required attachment members to its ends; in this embodiment these attachment members comprise a hook member 29 and an eyelet member 30 attached to respective ends. Referring now to FIGS. 2-4, an eyelet attachment member of the invention consists of a body having one end 32 of cylindrical shape while the other end has the shape of a thinner flattened tongue with a rounded end, the tongue having a cylindrical eyelet hole 34 formed therein. The cylindrical shape end 32 is provided with a coaxial cylindrical annular recess 36, so as to have a cylindrical annular collar portion 38 and a coaxial cylindrical boss portion 40, the dimensions of the recess and these portions being such that the recess 36 will snugly but easily receive the hollow spring end, the end embracing the boss portion and in turn being embraced by the collar portion. The boss end has a tapered conical nose that protrudes beyond the collar and facilitates its entry into the centre of the spring. Preferably the boss is a little larger in diameter than the spring recess so that the spring is expanded as it is pushed on to the boss.

The spring material is inherently a hard metal and the metal from which the attachment member is formed is much more ductile, to the extent that it can readily be compressed by squeezing radially inward to plastically deform it into the inner and outer grooves of the helical coil without deforming the coil spring, so that thereafter the eyelet is held securely on the end of the spring under the relatively small tension loads that are applied to it. A suitable material for the attachment member is for example 17-4 PH or 316 dead soft stainless steel. Owing to the small size of the member the force required for such plastic deformation is correspondingly small and if performed by the orthodonist can readily be applied using a pair of hand-operated pliers, preferably with the opposed jaws formed with cooperating semi-cylindrical recesses.

Figure 5:
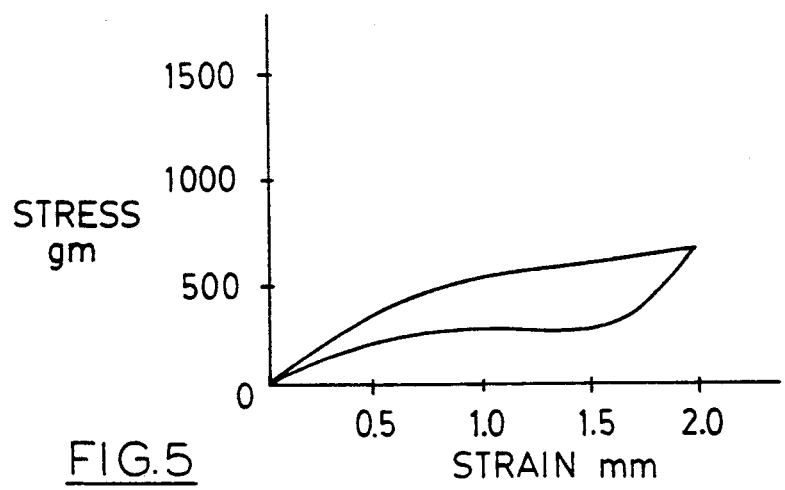
FIG. 5 is a simplified graph illustrating the stress/strain characteristic typical of nickel/titanium superelastic spring materials especially suitable for the manufacture of orthodontic traction springs of the invention.

A series of shape-memory nickel/titanium metal alloys, sometimes called "superelastic" alloys, have been developed for use in the fabrication of orthodontic springs having the stress/strain characteristic illustrated by FIG. 5. Thus, the tension required to stretch the spring increases progressively from zero elongation, as with springs of more usual metals, but very rapidly the characteristic becomes relatively very flat, so that the tension remains correspondingly constant irrespective of the degree of elongation, until the extension approaches the elastic limit of the material, which can be as much as 500%. It is therefore possible to provide springs having the required low tension characteristic over a wide range of movement, as is encountered in intermaxillary procedures, with the added advantage that because of the large extra elastic elongation that is possible it becomes unlikely that the spring can become over-stressed and weaken or fail. These spring materials are sold by Ortho Tony Inc., of Japan and springs fabricated from these materials are sold in North America by G.A.C. International Inc.

Typically the springs are fabricated from wire of 0.190 mm (0.0075 in) or 0.228 mm (0.009 in) diameter to have an inner coil diameter of 0.711 mm (0.028 in) or 0.812 mm (0.032 in). In a preferred embodiment where the coil uses the 0.228 mm wire and is of 0.812 mm inner diameter the overall length of the eyelet attachment member is 2.616 mm (0.103 in) and the outer diameter of the cylindrical end 28 is 1.625 mm (0.064 in). The annular recess 34 is 0.686 mm (0.027 in) deep, with an internal diameter (external for the boss portion 38) of 0.787 mm (0.031 in) and an external diameter (internal for the collar portion 36) of 1.213 mm (0.052 in), so that the spring end can easily be pushed therein and will remain in place by friction until it can be crimped in place. The thickness of the tongue 30 is 0.508 mm (0.020 in) while in this embodiment the eyelet hole 32 is relatively large, of 1.016 mm (0.040 in) diameter, so that it fits freely over the hooks and can easily be placed and removed, either by the orthodonist or by the patient.

The dimensions of the attachment members can of course vary somewhat from those of the preferred embodiment, but it is the constant endeavour in this field to make all components as small as possible because of their location in the mouth and the desire to avoid as much as possible any physical contact between the appliances, gums, mouth lining, etc. The dimensions are also dictated very considerably by the dimensions of the spring material with which it is to be used. For example, the outer diameter of the boss portion 38 could be increased to about 0.85 to 0.95 mm (0.034 to 0.038 in), which will somewhat increase the friction between the spring and the boss as the spring is inserted. The external diameter of the attachment body should then be increased correspondingly to about 1.65 to 1.70 mm (0.066 to 0.068 in).

Figure 6:
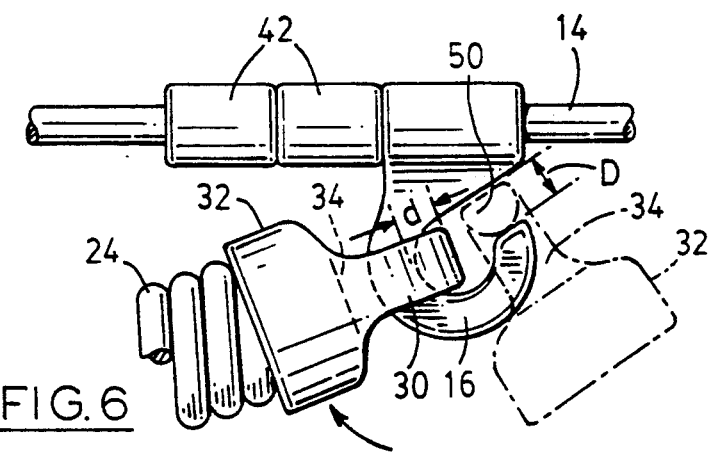
FIG. 6 is a side elevation view of the archwire hook anchor member of FIG. 1 in combination with an eyelet attachment member that is another embodiment of the invention, the combination permitting ready attachment and detachment of the eyelet to the hook by the orthodontist but not by a patient.
Figure 7:
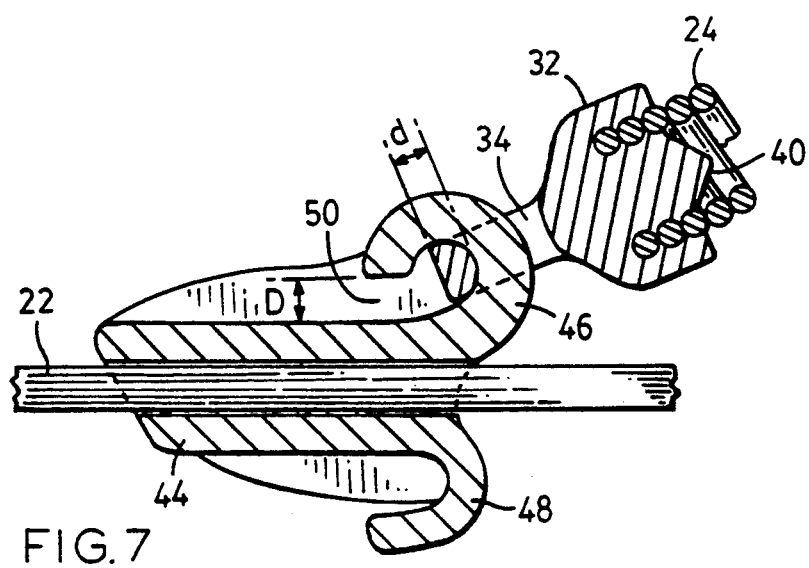
FIG. 7 is a cross section similar to FIG. 4 of a buccal tube and an eyelet attachment member similar to that of FIG. 6, showing the manner of employment of the attachment member in combination with a cooperating hook member on the buccal tube.
Figure 8:
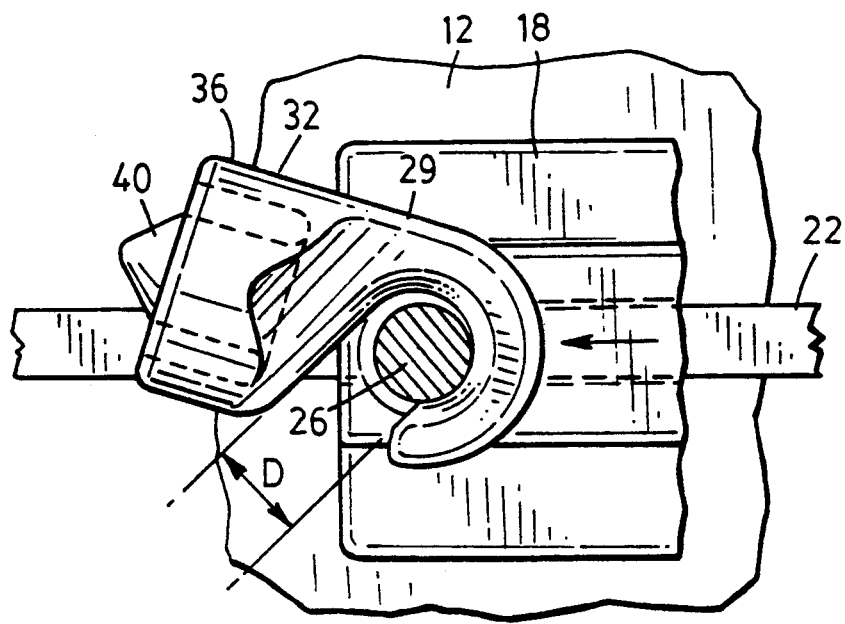
FIG. 8 is a part elevation, part cross-section, of a hooked attachment member of the invention illustrating its use in combination with a headed pin anchor member on a buccal tube.
Figure 9:
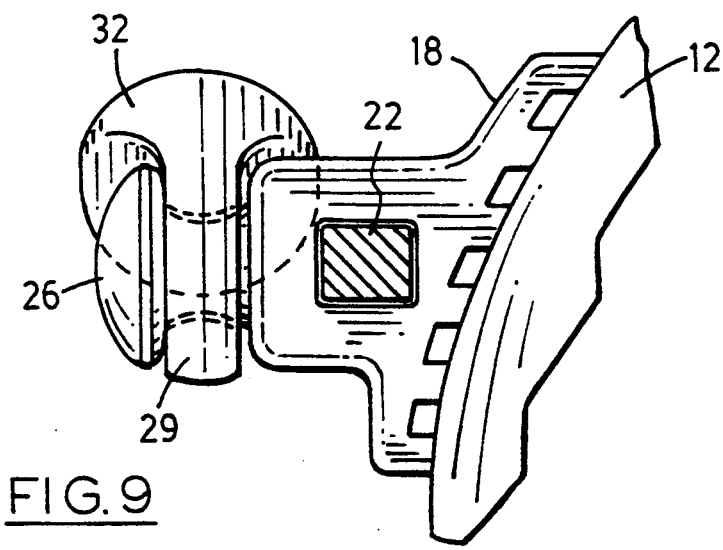
FIG. 9 is an end elevation of the hooked attachment member and buccal tube of FIG. 8.
Figure 10:
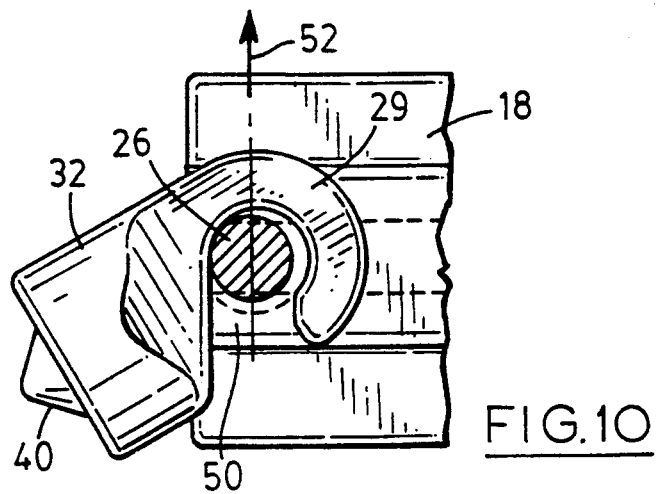
FIGS. 10 and 11 are views similar to FIG. 8 to show the two different angularities of the hooked attachment member relative to the buccal tube required to remove the attachment member from a headed pin anchor member on the buccal tube.
Figure 11:
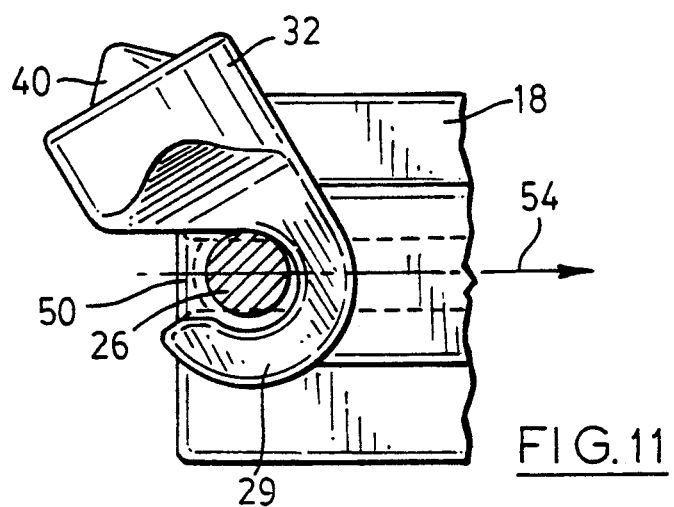

As described above, it is often found that the patient for various reasons disconnects the traction spring, and FIGS. 6 and 7 illustrate hook and eyelet combinations that inhibit this, while permitting the orthodonist to readily connect and disconnect the traction spring in the operatory. The eyelet embodiment illustrated in FIG. 6 is used in combination with the hook 16 which is held against endwise movement by stops 42, while as illustrated in FIG. 7 it used in combination with a buccal tube 44 mounted on arch wire 22 and having eyelet-receiving anchor member hook 46 and elastomer-receiving hook 48. The hook mouth or entrance 50 between the hook end and its body has a dimension D that is smaller than the thickness of the eyelet tongue, but which is larger than the longitudinal dimension d of the rear endmost portion of the tongue bordering the eyelet hole 34. It is not possible therefore to unhook the eyelet tongue from the hook by a simple linear extension and small rotation of the spring end, as with the previously described embodiment, and instead it can only be removed by first rotating the attachment member through a ninety degree angle from the position shown in FIG. 6 in solid lines to that shown in broken lines, when the member is in the required attitude and the dimension d of the border portion is appropriately aligned with the larger hook mouth dimension D, so that the border portion is able to pass through it. This will usually require the use of a gripping tool to hold the eyelet, which the average patient is unlikely to have available, and also involves stretching and bending the spring 24 to an extent which the average patient is unlikely to attempt, thinking that it will weaken or break it. Owing to the special characteristic of such spring materials this extreme bending and stretching is well within their capabilities without damage.

The eyelet attachment member 30 may be used at both ends of the spring connector member 24 or, as shown in FIG. 1 and illustrated to a larger scale in FIGS. 8–11, a hooked attachment member 29 may be used instead, the hook cooperating with the headed pin 26 on the buccal tube 18 in a manner described below to also inhibit its removal by the patient. It will be seen from FIG. 9 that the hook embraces the small diameter post or shaft of the pin and is rotatable thereon. The occlusal-gingival dimension of the part of the buccal tube body through which the arch wire 22 passes is about the same as that of the head of the pin 26, and it will be seen from FIG. 8 that it is not possible to remove the hook from the pin shaft while it is in the operative attitude of FIGS. 1 and 8, since the distal and occlusal movements required are prevented by the consequential physical engagement of the cylindrical body 32 with the end of the buccal tube. Thus, the hooked member can only be removed if it is either rotated to the attitude shown in FIG. 10, when it can be moved occlusally (arrow 52) with the attachment member body passing occlusally along the mesial end of the buccal tube, or alternatively is rotated to the attitude shown in FIG. 11, when it can be moved distally (arrow 54) with its body passing distally along the occlusal surface of the buccal tube. Both of these angulations are sufficiently extreme for it to be unlikely that they would be attempted by a patient, and also sufficient usually to require the use of a gripping tool for easy installation and removal.

Figure 12:
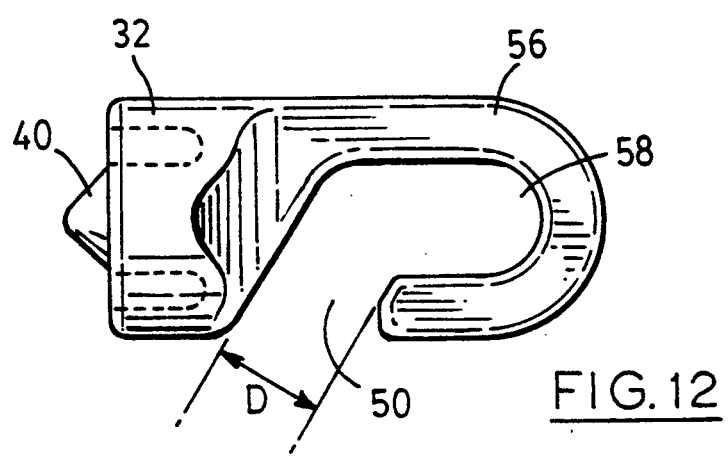
FIG. 12 illustrates another form of hooked attachment member of the invention.

A hooked attachment member 56 which is another embodiment of the invention is shown in FIG. 12, the hook being provided with a pin-receiving slot 58 that is elongated longitudinally of the member to provide for a small amount of mesial-distal movement of the member on the pin. As with the hook of the embodiment of FIGS. 8–11, because the entrance 50 to the hook slot is immediately adjacent to the member cylindrical body 32, it cannot be removed while in the operative attitude of FIG. 1, but only if rotated to either of the relatively extreme attitudes of FIGS. 10 or 11. The purpose of a hook that permits this longitudinal movement between the hook and its anchoring pin is explained below in connection with FIG. 16.

Figure 13:
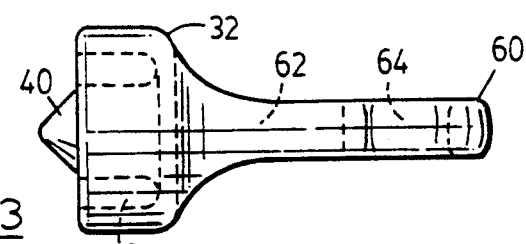
FIGS. 13 and 14 are side and top elevations respectively illustrating another form of eyelet attachment member of the invention.
Figure 14:
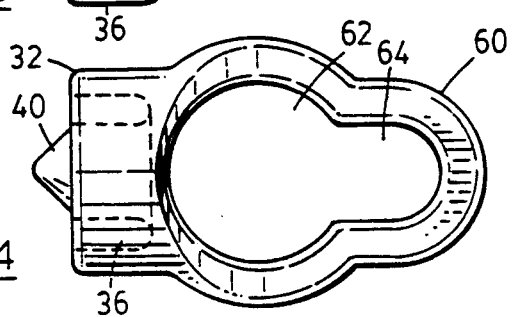

FIGS. 13 and 14 show another form of eyeletted attachment member 60 that can be used with the headed post 26 of the buccal tube 18, or with a similar headed post if provided on any of the other orthodontic devices, such as on a bracket. The tongue is flattened and the eyelet hole in the tongue is elongated longitudinally of the member so as to comprise an enlarged part 62 immediately adjacent the cylindrical body 32 that is of large enough diameter to allow the post head to pass freely through it; the hole also comprises a smaller diameter portion 64 further from the body 32 that will not allow the head to pass but freely embraces and is rotatable on the pin. The tension of the spring connector member urges the member mesially and holds the smaller diameter portion 64 in engagement with the pin post, so that it cannot be removed from the pin. This attachment can be removed relatively readily by the patient and therefore preferably is used only when this is permissible.

Figure 15:
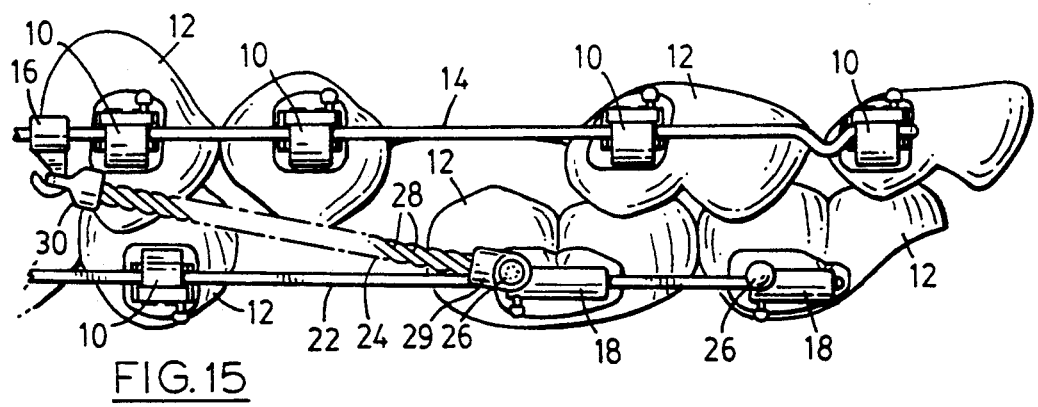
FIGS. 15 and 16 are two different buccal elevations similar to FIG. 1 showing a traction member of the invention employing a wire rope as the connection member.
Figure 16:
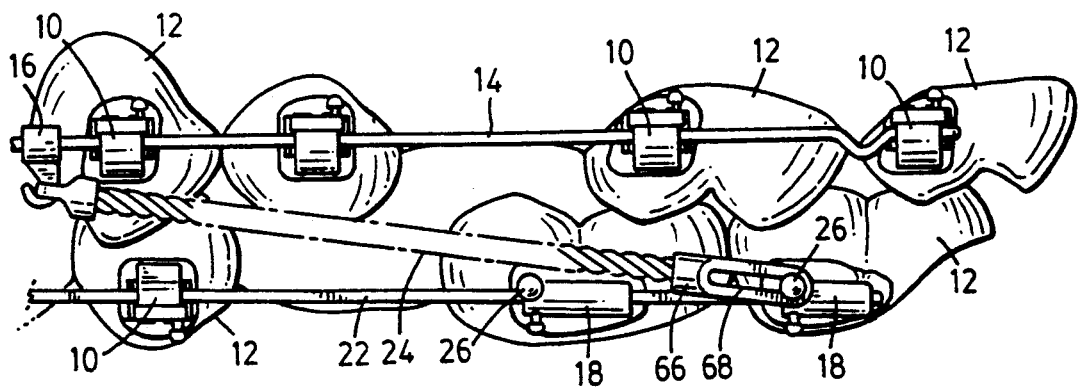

FIGS. 15 and 16 illustrate the structure and operation of two respective traction devices of the invention in which the connection member 24 between the eyelet attachment member 30 and the hooked attachment member 29 is an "inactive" member, as contrasted with the "active" helical spring member 24. A particular preferred material for this member is wire rope in that this multi-strand is strong and flexible and also, as with the helical spring, has a plurality of helical external grooves 28 into which an adhesive material can enter, or into which the material of the body 32 is forced by crimping, so as to facilitate the retention of the connection member in the attachment members. A suitable material is for example the stainless steel wire rope of about 0.813 mm (0.032 in) diameter sold by Winifred Berg of East Rockway, N.Y. Since the wire rope is solid throughout its cross section the recess 36 is cylindrical and not annular.

FIG. 16 also illustrates another attachment member 66 for attaching one end of the inactive connection member to a headed pin, this member permitting a predetermined amount of mesial-distal movement of the anchor member on the pin post, as compared to the equivalent hook and post structure 26,29 of FIG. 15. Thus, the member 66 has a mesial-distal longitudinally extending slot 68 of occlusal-gingival dimension large enough for it to slide freely on the pin post, but not large enough to allow the pin head to pass through, the member being mounted on the pin in a manner described below, so as to permit the attachment member to be connected to the post. The device of FIG. 15 does not allow the patient to extend the mandible because the connection member is inextensible once it has become taut, while the device of FIG. 16 permits the possibility of some functional protrusion, for example during eating.

Figure 17:
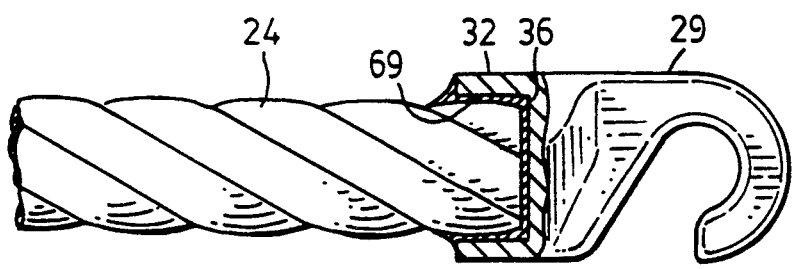
FIG. 17 is a part elevation, part cross-section, illustrating a method of attachment of a wire rope connection member to a hooked attachment member.

FIG. 17 illustrates another method of attaching one end of the solid cross-section wire rope connector member to a hook attachment member 29, namely by means of a layer 69 of fusible metal, such as brazing metal, or of a high-strength inert adhesive, such as an epoxy resin.

Figure 18:
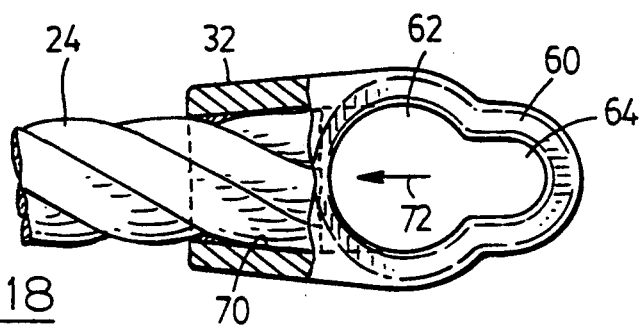
FIG. 18 is also a part elevation, part cross-section, illustrating another method of attachment of a wire rope connection member to an eyelet attachment member.

FIG. 18 illustrates another method of attaching one end of a wire rope connecting member 24 to an attachment member, the method being illustrated in connection with an eyeletted member 60. The cylindrical body portion 32 is hollow with a bore 70 that tapers with an inside diameter that reduces away from the tongue further end 60 and toward the connection member 24. The end of the rope within the bore 70 is splayed radially outwards to increase the size of the helical grooves after the rope has been fed endwise through the bore in the direction of the arrow 72, and the larger recesses thus formed are filled with a fusible metal or with a resin, so that the rope end is thereafter retained securely in the bore.

Figure 19:
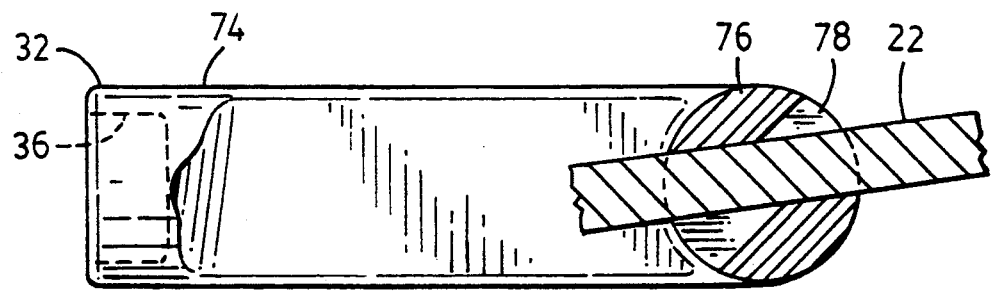
FIGS. 19 and 20 are respectively a side elevation with part cross sectioned and a top elevation of another form of attachment member of the invention to permit a traction device to be connected to an arch wire.
Figure 20:
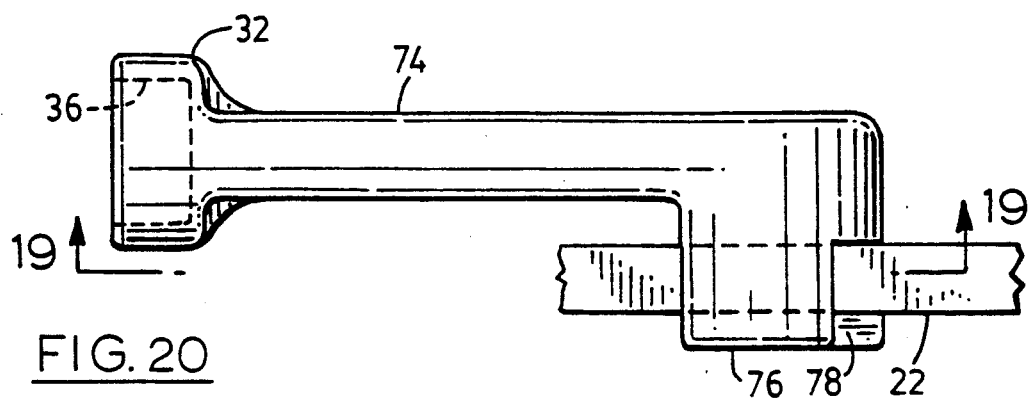

FIGS. 19 and 20 illustrate another attachment member 74 for attachment to one end of a traction device of the invention and for attachment in turn to an arch wire, the member illustrated being intended for use with a wire rope connecting member 24, but also being usable with a helical spring. The body of the device is elongated in the mesial-distal direction and its end further from the cylindrical body 32 is provided with a labially-protruding cylindrical boss 76 through which passes an arch wire passage 78 for reception of the arch wire. The two ends of this passage are tapered inwards toward each other to meet at two generally opposed labial-lingual extending rounded edges defining a passage of dimensions such that the arch wire slides freely with a limited transverse play. Thus, the device is free to slide distally along the arch wire 22 if the mandible is further protruded, as during function, the extent of the movement permitted along the arch wire being determined by its contact with the brackets or buccal tubes also on the wire, or with strategically placed stops such as the stops 42 of FIG. 6 mounted on the wire.

The geometry of the inwardly tapered slot allows approximately 30 degrees of occluso-gingival rotation and also sufficient bucco-lingual rotation. The cylindrical boss is placed in position between the devices that are to act as its stops and the arch wire threaded through; the resultant traction device does not interfere with the desired additional protrusion of the mandible over a considerable range in view of the fact there is always a relatively long span of arch wire between, for example, the buccal tubes on the first and second molars by which the attachment member is confined. Without this freedom to protrude the mandible the wire rope connector member would need to bow and flex during functional movements with increased possibility of fatigue failure.

Figure 21:
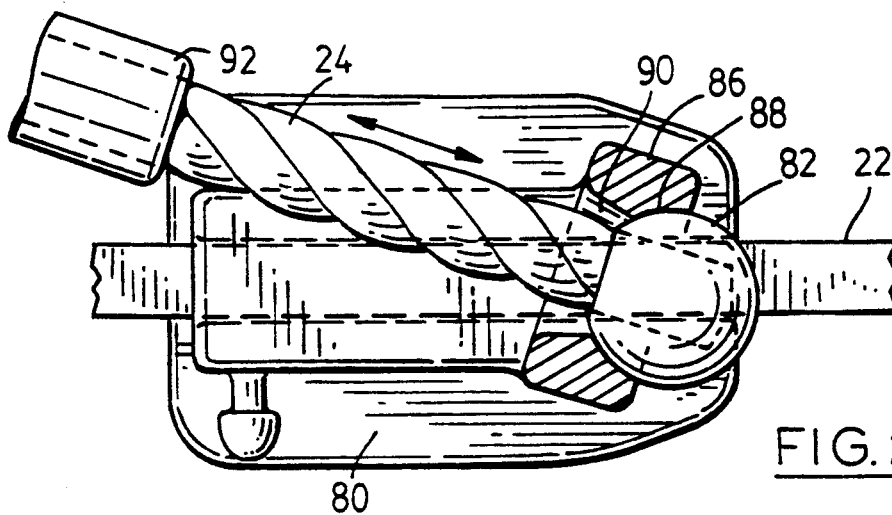
FIG. 21 is a buccal view of a another form of intermaxillary device of the invention comprising a buccal tube anchor member in combination with a wire rope connection member terminating in a spherical attachment member.
Figure 22:
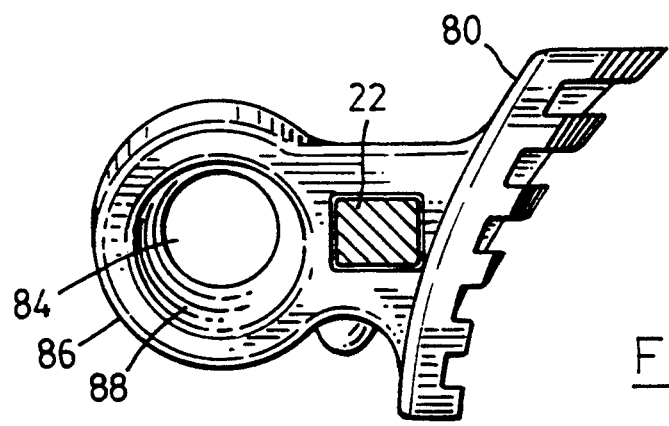
FIG. 22 is a view from the distal of the buccal tube alone of FIG. 21.

FIGS. 21 and 22 illustrate another traction device of the invention comprising an attachment member of new form that cooperates with a new anchor member comprising part of a buccal tube 80 through which the arch wire 22 passes. A wire rope connector member 24 is employed and the attachment member on one end is a spherical ball 82 into which the connector member 24 protrudes to be fastened therein, as by the method illustrated by FIG. 18, the far end of the bore being closed with the adhesive material and the outer surface of the ball being rendered smooth and spherical. The connector member passes freely through a bore 84 in a labially protruding body portion 86 of the buccal tube, the distal end 88 of the bore being hemi-spherical to form a cup that receives and mates with the adjacent hemi-spherical surface of the spherical ball 82, which can therefore swivel freely therein. The mesial end 90 of the bore is tapered outwardly mesially to permit the desired occluso-gingival and bucco-lingual rotations. The centre portion of the length of the wire rope connection member is provided with a smooth plastic coating 92, where it may contact the gums and mouth lining, the uncovered portion immediately adjacent the ball being of sufficient length to permit the required distal travel of the ball away from the surface 88 during functional movements of the mandible. With a wire rope 24 of 0.812 mm (0.032 in) diameter the ball 82 will be about 1.372 mm (0.054 in) diameter.

Figure 23:
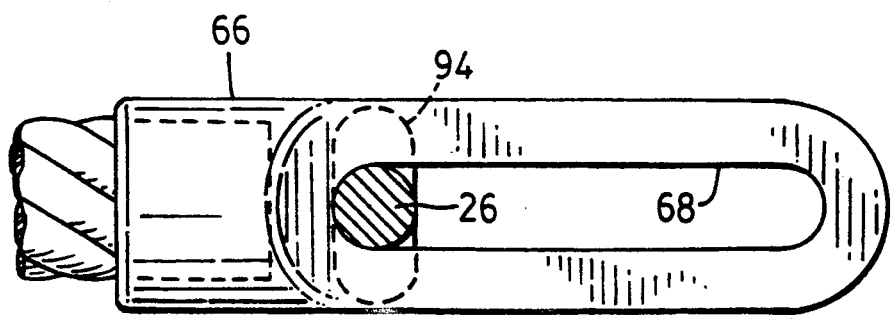
FIG. 23 is a side elevation of an attachment member with an elongated slot as shown in FIG. 16 and prior to mounting it on a T-headed pin anchor.

FIG. 23 illustrates one manner of mounting the attachment member 66 of FIG. 16 on a headed pin anchor member 26 provided with a head 94 that together with its shaft is of T-shape in one plane that is also a transverse cross-section. The width of the head at right angles to that plane is just sufficient for the head to pass through the slot 68 when the longer dimension of the head is aligned with the longer dimension of the slot, but the head is retained if there is even a small misalignment between these longitudinal dimensions. As with other embodiments therefore the member can only be mounted on the pin and removed therefrom when they are in two predetermined orientations, in this case two orientations at 180 degrees to one another, both of which will require an extensive amount of rotation of the member relative to the pin and consequent deformation of the connector member from its normal shape.

Figure 24:
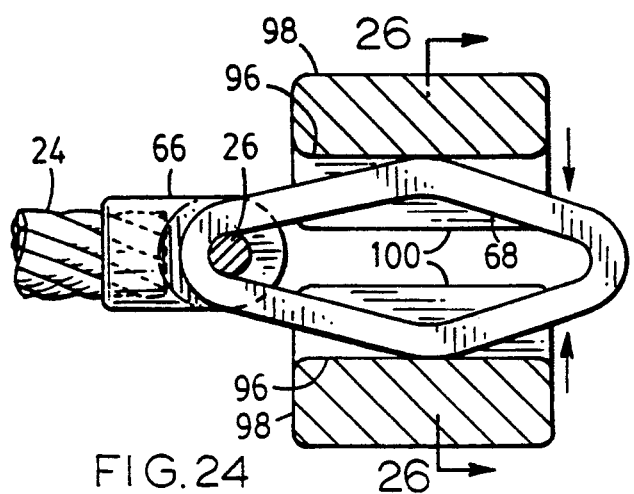
FIG. 24 is a side elevation of an another attachment member with an elongated slot prior to mounting it on a headed pin anchor, showing also a pair of jaws of a tool for mounting the attachment member on the post by crimping it.
Figure 26:
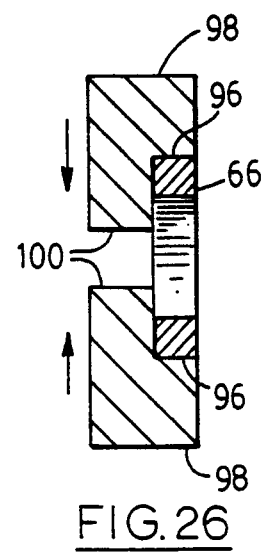
FIG. 26 is a section on the line 26—26 in FIG. 24.
Figure 25:
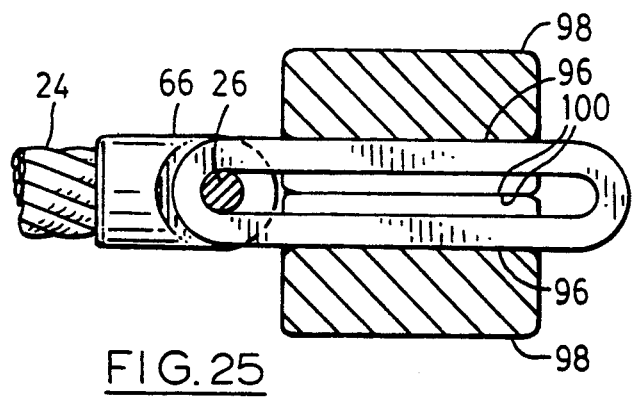
FIG. 25 is a side elevation similar to FIG. 24 showing the attachment member after its mounting on the post by the crimping.

FIGS. 24–26 illustrate another manner of mounting the attachment member 66 of FIG. 16 on the headed pin anchor member 26 when the slot 68 is again too small for the head of the pin to pass through. As shown in FIGS. 24 and 26 the attachment member is produced with the slot enlarged transversely to be of approximately oval shape with its width at the minor axis just enough to permit the head of the pin to pass through it. Thereafter, with the pin in place the orthodontist applies the beak surfaces 96 of a pair of jaws 98 to the opposite sides of the device and squeezes to crimp the member and move the two sides toward one another until the jaw stop surfaces 100 meet, when the sides of the slot will be parallel and able to retain the headed pin therein while also permitting the pin to slide freely along the length of the slot. Removal of the device will entail its destruction by cutting through one side of the member and bending the separated parts until the head passes through the resultant gap.

I claim:

1. An orthodontic traction device comprising a connection member constituted by a length of connection material which is a piece of hollow helical coiled spring having helical grooves in both its interior and exterior cylindrical surfaces between the butting coils of the spring and two end attachment members attached respectively at its two ends:

each attachment member comprising a body having at one end thereof an attachment means for its attachment to an orthodontic anchor member, and having at another end thereof a collar portion having an annular body recess formed therein between the collar portion and a cylindrical inner body boss portion, the recess being of radial dimension sufficient to snugly receive therein the respective end of the connection member with the collar portion embracing the connection member end and with the connection member end embracing the inner body boss portion;

the attachment member being attached to the connection member by material of the body radially compressed inwards into the portions of said helical grooves of the connection member end within the recess in both the interior and exterior cylindrical surfaces thereof;

the attachment being such as to prevent withdrawal of the connection member end from the body recess under tension applied to or by the device.

2. A device as claimed in claim 1, wherein an end of the boss protrudes from the body, and the protruding end has a tapered nose facilitating its insertion into the interior of the hollow spring material.

3. A device as claimed in claim 1, wherein the boss portion is slightly larger in external diameter than the interior diameter of the hollow spring material, so that insertion of the boss portion into the interior of the spring material causes radially outward expansion thereof and increases the frictional engagement between them.

4. A device as claimed in claim 1, wherein the attachment member body has a tongue shaped extension in which the attachment means is formed.

5. A device as claimed in claim 4, in combination with a hook member to which an attachment member thereof is to be attached;

wherein the attachment means comprises an eyelet hole in the tongue extension;

wherein the thickness of the tongue shaped extension is greater than the height dimension of the hook member mouth; and wherein the width of the endmost portion of the tongue which borders the eyelet hole is less than the height dimension of the hook member mouth, so that the attachment member can only be mounted on and dismounted from the hook member with the attachment member in the attitude required to present the tongue shaped extension border to the height dimension of the hook member mouth.

6. A device as claimed in claim 4, wherein the attachment means comprises a hook formed in the tongue shaped extension.

7. A device as claimed in claim 6, in combination with another orthodontic device having a headed pin with a smaller diameter shaft as an anchor member;

wherein the attachment member body is wider in the labial-lingual direction than the hook to have at least a body portion that protrudes lingually beyond the hook;

wherein said another orthodontic device has a body with a labially protruding portion;

and wherein dismounting of the hook from the headed pin is prevented by engagement of the lingually-protruding portion of the attachment member body with the labially protruding portion of the body of the other device unless the hook is in a predetermined angulation relative to the last mentioned body.

8. A device as claimed in claim 7, wherein the shaft receiving slot is elongated in the longitudinal direction to permit corresponding longitudinal movement of the hook on the shaft of the headed pin.

9. A device as claimed claim 1, in combination with another orthodontic device having a headed pin with a smaller diameter shaft as an anchor member;

wherein the attachment means comprises an eyelet hole having a portion of enlarged diameter adjacent to the collar portion through which the head of the headed pin can pass, the eyelet hole having a portion of smaller diameter further from the collar portion through which the head cannot pass but in which the smaller diameter shaft of the headed pin can move longitudinally.

10. A device as claimed in claim 1, in combination with another orthodontic device having a headed pin with a smaller diameter shaft as an anchor member, wherein an eyelet hole provided in the attachment member is elongated in the longitudinal direction to permit corresponding longitudinal movement of the attachment member of the shaft of the headed pin.

11. A device as claimed in claim 10, wherein the the headed pin is of T-shape in transverse cross-section in one plane with the width of the head sufficient to permit it to pass through the hole while the longer dimension of the cross-bar of the T-shape is aligned with the longer dimension of the hole, the length of the cross bar being such that the device is retained by the head of the pin when it is not so aligned, the width of the hole also being such as to permit the smaller diameter shaft to move freely longitudinally therein.

12. A device as claimed in claim 10, wherein the attachment member is made with the central portion of the elongated eyelet hole of sufficient width to permit the head of the pin to pass through, the longitudinal sides of the attachment member bordering the hole thereafter being squeezed by crimping to move them toward one another and reduce the width of the central portion until it retains the head of the pin while permitting the smaller diameter shaft to move freely longitudinally therein.

13. A device as claimed in claim 12, in combination with a squeezing tool for squeezing together the longitudinal sides of the attachment member, the tool having spaced jaws having beak surfaces for engaging the longitudinal sides and having stop surfaces which are engaged when the beak surfaces are spaced the required distance apart.

14. A device as claimed in claim 1, wherein the attachment member body is provided adjacent one end with a lingually extending protrusion and a mesially-distally extending arch wire receiving passage is provided in the protrusion.

15. A device as claimed in claim 14, wherein the arch wire receiving passage tapers inwardly from both its ends to be of smaller occlusal-gingival dimension intermediate its ends.

16. A device as claimed in claim 1, wherein the attachment member body is spherical and the attachment means thereof comprises a hemispherical surface of the body, and wherein an associated anchor member has a mesial-distal extending passage through which the connector member passes and a distal-opening hemispherical cup into which the spherical body enters to limit the relative mesial-distal movement of the connector and anchor members, while permitting angulation of the connector member relative to the anchor member.

17. A device as claimed in claim 1, in combination with a hook member having a hook member mouth and to which an attachment member thereof is to be attached, and also in combination with another orthodontic device having a headed pin with a smaller diameter shaft as an anchor member to which the device is to be attached;

the device having at one end an eyelet attachment device and at the other end a hook attachment device;

the eyelet attachment device comprising an attachment member body having a tongue shaped extension with an eyelet hole therein, the thickness of the tongue shaped extension being greater than the height dimension of the hook member mouth;

the width of the endmost portion of the tongue which borders the eyelet hole being less than the height dimension of the hook member mouth, so that the attachment member can only be mounted on and dismounted from the hook member with the attachment member in the attitude required to present the tongue shaped extension border to the height dimension of the hook member mouth;

the hook attachment device having a hook opening comprising a shaft-receiving slot, the attachment member body being wider in the labial-lingual direction than the hook to have at least a body portion that protrudes lingually beyond the hook, and said another orthodontic device having a body with a labially protruding portion;

wherein dismounting of the hook from the headed pin is prevented by engagement of the lingually-protruding portion of the attachment member body with the labially protruding portion of the body of the other device unless the hook is in a predetermined angulation relative to the last mentioned body.

18. An orthodontic traction device comprising a connection member constituted by a piece of multi-strand wire rope connection material having exterior helical grooves formed between the abutting strands thereof in its exterior cylindrical surface and two end attachment members attached respectively at its two ends:

each attachment member comprising a body having at one end thereof an attachment means for its attachment to an orthodontic anchor member, and having at another end thereof a collar portion having a cylindrical body recess formed therein, the recess being or radially dimension sufficient to snugly receive therein the respective end of the connection member with the collar portion embracing the connection member end;

the attachment member being attached to the connection member by an interposed adhesive material which has entered into the portions of said helical grooves of the connection member end within the recess;

the attachment being such as to prevent withdrawal of the connection member end from the body recess under tension applied to or by the device.

19. A device as claimed in claim 18, wherein the attachment member body has a tongue shaped extension in which the attachment means is formed.

20. A device as claimed in claim 19, in combination with a hook member to which an attachment member thereof is to be attached;

wherein the attachment means comprises an eyelet hole in the tongue extension;

wherein the thickness of the tongue shaped extension is greater than the height dimension of the hook member mouth; and wherein the width of the endmost portion of the tongue which borders the eyelet hole is less than the height dimension of the hook member mouth, so that the attachment member can only be mounted on and dismounted from the hook member with the attachment member in the attitude required to present the tongue shaped extension border to the height dimension of the hook member mouth.

21. A device as claimed in claim 19, wherein the attachment means comprises a hook formed in the tongue shaped extension.

22. A device as claimed in claim 21, in combination with another orthodontic device having a headed pin with a smaller diameter shaft as an anchor member;

wherein the hook opening comprises a shaft-receiving slot;

wherein the attachment member body is wider in the labial-lingual direction than the hook to have at least a body portion that protrudes lingually beyond the hook;

wherein said another orthodontic device has a body with a labially protruding portion;

and wherein dismounting of the hook from the headed pin is prevented by engagement of the lingually-protruding portion of the attachment member body with the labially protruding portion of the body of the other device unless the hook is in a predetermined angulation relative to the last mentioned body.

23. A device as claimed in claim 22, wherein the shaft receiving slot is elongated in the longitudinal direction to permit corresponding longitudinal movement of the hook on the shaft of the headed pin.

24. A device as claimed in claim 18, in combination with another orthodontic device having a headed pin with a smaller diameter shaft as an anchor member;

wherein the attachment means comprises an eyelet hole having a portion of enlarged diameter adjacent to the collar portion through which the head of the headed pin can pass, the eyelet hole having a portion of smaller diameter further from the collar portion through which the head cannot pass but in which the smaller diameter shaft of the headed pin can move longitudinally.

25. A device as claimed in claim 18, in combination with another orthodontic device having a headed pin with a smaller diameter shaft as an anchor member, wherein an eyelet hole provided in the attachment member is elongated in the longitudinal direction to permit corresponding longitudinal movement of the attachment member on the shaft of the headed pin.

26. A device as claimed in claim 25, wherein the the headed pin is of T-shape in transverse cross-section in one plane with the width of the head sufficient to permit it to pass through the hole while the longer dimension of the cross-bar of the T-shape is aligned with the longer dimension of the hole, the length of the cross bar being such that the device is retained by the head of the pin when it is not so aligned, the width of the hole also being such as to permit the smaller diameter shaft to move freely longitudinally therein.

27. A device as claimed in claim 25, wherein the attachment member is made with the central portion of the elongated eyelet hole of sufficient width to permit the head of the pin to pass through, the longitudinal sides of the attachment member bordering the hole thereafter being squeezed by crimping to move them toward one another and reduce the width of the central portion until it retains the head of the pin while permitting the smaller diameter shaft to move freely longitudinally therein.

28. A device as claimed in claim 27, in combination with a squeezing tool for squeezing together the longitudinal sides of the attachment member, the tool having spaced jaws having beak surfaces for engaging the longitudinal sides and having stop surfaces which are engaged when the beak surfaces are spaced the required distance apart.

29. A device as claimed in claim 18, wherein the attachment member body is provided adjacent one end with a lingually extending protrusion and a mesially-distally extending arch wire receiving passage is provided in the protrusion.

30. A device as claimed in claim 29, wherein the arch wire receiving passage tapers inwardly from both its ends to be of smaller occlusal-gingival dimension intermediate its ends.

31. A device as claimed in claim 18, wherein the attachment member body is spherical and the attachment means thereof comprises a hemispherical surface of the body, and wherein an associated anchor member has a mesial-distal extending passage through which the connector member passes and a distal-opening hemispherical cup into which the spherical body enters to limit the relative mesial-distal movement of the connector and anchor members, while permitting angulation of the connector member relative to the anchor member.

32. A device as claimed in claim 18, wherein the wire rope connector member is coated with a plastic material.

33. A device as claimed in claim 18, in combination with a hook member having a hook member mouth and to which an attachment member thereof is to be attached, and in combination with another orthodontic device having a headed pin with a smaller diameter shaft as an anchor member to which the device is to be attached;

the device having at one end an eyelet attachment device and at the other end a hook attachment device;

the eyelet attachment device comprising an attachment member body having a tongue shaped extension with an eyelet hole therein, the thickness of the tongue shaped extension being greater than the height dimension of the hook member mouth;

the width of the endmost portion of the tongue which borders the eyelet hole being less than the height dimension of the hook member mouth, so that the attachment member can only be mounted on and dismounted from the hook member with the attachment member in the attitude required to present the tongue shaped extension border to the height dimension of the hook member mouth;

the hook attachment device having a hook opening comprising a shaft-receiving slot, the attachment member body being wider in the labial-lingual direction than the hook to have at least a body portion that protrudes lingually beyond the hook, and said another orthodontic device having a body with a labially protruding portion;

wherein dismounting of the hook from the headed pin is prevented by engagement of the lingually-protruding portion of the attachment member body with the labially protruding portion of the body of the other device unless the hook is in a predetermined angulation relative to the last mentioned body.

34. A device as claimed in claim 18, wherein the strands of the multi-strand wire rope within the respective attachment member are splayed radially outwards to increase the size of the helical grooves prior to the interposition of adhesive material therein for its attachment to the attachment member.

* * * * *